US012521528B2

(12) United States Patent
Coll Pérez et al.

(10) Patent No.: US 12,521,528 B2
(45) Date of Patent: Jan. 13, 2026

(54) SANITARY DRESSING

(71) Applicant: IBERHOSPITEX, S.A., Lliçà de Vall (ES)

(72) Inventors: Marc Coll Pérez, Lliçà de Vall (ES); Christian Breu, Putzbrunn (DE); Mario López Moya, Lliçà de Vall (ES)

(73) Assignee: IBERHOSPITEX, S.A., Lliçà de Vall (ES)

( * ) Notice: Subject to any disclaimer, the term of this patent is extended or adjusted under 35 U.S.C. 154(b) by 942 days.

(21) Appl. No.: 17/762,005

(22) PCT Filed: Sep. 18, 2020

(86) PCT No.: PCT/EP2020/076167
§ 371 (c)(1),
(2) Date: Mar. 18, 2022

(87) PCT Pub. No.: WO2021/053179
PCT Pub. Date: Mar. 25, 2021

(65) Prior Publication Data

US 2022/0355079 A1 Nov. 10, 2022

(30) Foreign Application Priority Data

Sep. 20, 2019 (EP) .................................... 19382813

(51) Int. Cl.
*A61M 25/02* (2006.01)

(52) U.S. Cl.
CPC ..... *A61M 25/02* (2013.01); *A61M 2025/0246* (2013.01); *A61M 2025/0266* (2013.01)

(58) Field of Classification Search
CPC .......... A61M 25/02; A61M 2025/0246; A61M 2025/0266; A61F 2013/00412
See application file for complete search history.

(56) References Cited

U.S. PATENT DOCUMENTS

| | | | |
|---|---|---|---|
| 5,415,642 | A | 5/1995 | Shepherd |
| 2008/0208145 | A1 | 8/2008 | McCulloch |

(Continued)

FOREIGN PATENT DOCUMENTS

| | | | |
|---|---|---|---|
| EP | 0671182 | A * | 9/1995 |
| EP | 0671182 | A1 | 9/1995 |

(Continued)

OTHER PUBLICATIONS

International Search Report mailed Dec. 23, 2020 Application No. PCT/EP2020/076167, 5 pages.

(Continued)

*Primary Examiner* — Theodore J Stigell
(74) *Attorney, Agent, or Firm* — SQUIRE PATTON BOGGS (US) LLP

(57) ABSTRACT

A sanitary dressing for protecting a portion of a catheter protruding from a patient body through a skin entry site is provided. The sanitary dressing comprises a proximal zone to be arranged on a primary dressing which is in contact with patient skin, a distal zone and an intermediate zone between the proximal and distal zones, thereby forming a sheath for receiving the portion of the catheter. The proximal zone comprises an adhesive compatible with polyurethane for enabling repositioning of the sanitary dressing on the primary dressing.

20 Claims, 2 Drawing Sheets

(56) References Cited

U.S. PATENT DOCUMENTS

| | | | | |
|---|---|---|---|---|
| 2010/0294286 | A1* | 11/2010 | Bellamy | A61M 25/02 128/887 |
| 2012/0067896 | A1 | 3/2012 | Daffner et al. | |
| 2012/0283615 | A1 | 11/2012 | Malik et al. | |
| 2012/0298114 | A1 | 11/2012 | Landsman et al. | |
| 2015/0257833 | A1* | 9/2015 | Dabel | A61M 39/20 604/171 |
| 2019/0092982 | A1 | 3/2019 | Wu et al. | |

FOREIGN PATENT DOCUMENTS

| | | | |
|---|---|---|---|
| EP | 2982355 | A1 | 2/2016 |
| EP | 3378451 | A1 | 9/2018 |
| JP | H06105857 | A | 4/1994 |
| JP | 2018000956 | A | 1/2018 |
| JP | 3215411 | U | 3/2018 |
| WO | 2016/046286 | A1 | 3/2016 |

OTHER PUBLICATIONS

Written Opinion of the International Searching Authority mailed Dec. 23, 2020 Application No. PCT/EP2020/076167, 6 pages.

* cited by examiner

SANITARY DRESSING

CROSS-REFERENCE TO RELATED APPLICATIONS

This application is a national-stage filing under 37 USC 371(c) of International Application No. PCT/EP2020/076167, filed Sep. 18, 2020, which claims priority to, and the benefit of, European Patent Application 19382813, filed Sep. 20, 2019. The entire contents of each of these applications are herein incorporated by reference in their entirety for all purposes.

This application claims the benefit of European Patent Application EP19382813 filed on Sep. 20, 2019.

The present disclosure relates to sanitary dressings, more specifically to sanitary dressings for protecting a protruding portion of a catheter inserted into a patient body.

BACKGROUND

During medical care of patients, catheters may be used to access the circulatory system for the purposes of blood extraction, hydration of the patient, administering of medication and kidney dialysis, among others.

A catheter may typically include an insertion end that penetrates into the patient's circulatory system through an orifice in the skin, i.e. the skin entry site, a valve mechanism that closes the access to e.g. the vein when the device is not in use, and a connection port that remains outside the body and allows the connection of an external device such as an IV (intravenous) drip source, syringe, etc. Such a catheter may remain in the body for an extended period of time, and, in order to protect the skin entry site, i.e. an open wound, it is known to use a primary self-adhesive sanitary dressing to fix the catheter, cover the skin entry site, prevent infections and improve patient comfort. In some cases, the protruding or exposed portion of the catheter i.e. the part not covered by the primary dressing, may remain uncovered, however, this may lead to infections and to discomfort of the patient.

In other cases, in addition to the primary dressing adhered on the skin entry site, the protruding portion of the catheter may be wrapped in a sterile gauze in order to prevent infections. However, the protruding portion of the catheter may need to be accessed for treatment. Therefore, each time the catheter is to be accessed, the whole gauze must be removed which is time consuming and may also cause discomfort to the patient.

Furthermore, known dressings comprise adhesives to ensure a proper fixation to the patient skin, e.g. to avoid undesired movements or even to avoid accidental detachment. However, using strong adhesives may result in an over-attachment of the dressing that may not only make difficult the removal of the dressing and cause pain and/or discomfort to the patient but may even damage the patient upon removal. In addition, an over-attachment of the adhesive to patient skin, may also cause the separation of the different layers of the sanitary dressing as a consequence of the pulling force upon detachment.

Furthermore, the adhesive may not let the patient skin to breathe which may result in an excessive transpiration that may cause irritation and discomfort.

US2015257833 A1 discloses a catheter covering device with a sleeve and an adhesive film.

US2008208145 A1 discloses a disposable shower guard for renal access catheter.

EP0671182 A1 discloses a catheter protector.

EP3378451 A1 discloses a sanitary dressing for protecting a protruding portion of a catheter implanted into a patient body.

In conclusion, it may be convenient to provide a sanitary dressing that protects the protruding portion of the catheter, facilitates the access to such protruding portion for treatment and ensures a proper fixation as well as an easy removal, while at the same time maintains the integrity upon removal and improves patient comfort.

SUMMARY

In a first aspect, a sanitary dressing for protecting a portion of a catheter protruding from a patient body through a skin entry site is provided. The sanitary dressing comprises a proximal zone to be arranged on a primary dressing which is in contact with patient skin, a distal zone and an intermediate zone between the proximal and distal zones, thereby forming a sheath for receiving the portion of the catheter. The proximal zone comprises an adhesive compatible with polyurethane, or with a polyurethane film dressing, for enabling repositioning of the sanitary dressing on the primary dressing.

By using a primary dressing together with a sanitary dressing enables protecting simultaneously and separately the skin entry site and the protruding portion of the catheter. That is, on the one hand the risk of infection at the exposed catheter portion i.e. the protruding portion, is prevented or at least substantially reduced and on the other hand, the skin entry site may be covered and protected for longer periods i.e. as the primary dressing may remain in place for longer periods, which improves the comfort of the patient.

In addition, the use of a polyurethane compatible adhesive at the sanitary dressing prevents a tight fixation to the primary dressing. The sanitary dressing may easily be detached from the primary dressing without causing the detachment of the primary dressing and/or without causing discomfort to the patient. In the event the sanitary dressing is not properly arranged, it may be removed and re-positioned until a proper arrangement is achieved. A repositionable sanitary dressing may therefore be obtained.

In addition, as the sanitary dressing is independent from the primary dressing, it may be separately disposed e.g. in the event it is stained by blood or moisten by fluids leaking from the catheter.

In some examples, adhesive may only cover part of the surface of the proximal zone. Therefore, when adhering the proximal zone to the primary dressing, the breathability of the primary dressing may not be reduced.

In an example, sheath may comprise a first opening arranged between the proximal zone and the intermediate zone for enabling the portion of the catheter protruding from the skin entry site to be received in the sheath, and a detachable joint closing the distal zone and forming a second opening upon detachment.

The provision of a detachable joint having a closing mechanism enables gaining access to the catheter, for example for treatment, without removing the entire dressing, thereby the skin entry site and the catheter protruding from the patient body are not unnecessarily exposed and the risk of infection is therefore reduced.

Additionally, in case the catheter needs to be accessed "urgently", e.g. quickly, there is no need to rapidly detach the whole sanitary dressing from the patient skin to access the protruding portion of the catheter as the detachable joint provides an easy and fast access while the dressing is still adhered to the skin. The risk of injuring the patient by a rapid removal of the dressing, in case an urgent access is required, is prevented. The patient comfort may therefore be enhanced as unpleasant removals are prevented.

In some examples, the sanitary dressing may comprise an exterior sheet and an interior sheet joined by joints in the intermediate zone and in the distal zone thereby forming the sheath.

In some examples, wherein the joints of the distal zone may be different from the joints of the intermediate zone, preferably weaker, such that the joints of the intermediate zone form stops that limit the aperture of the second opening upon detachment of the detachable joint. Comprising different type of joints may lead to a dressing having bonds of different strength, i.e. some joints may be weaker or easier to decouple e.g. the joints forming the detachable opening, and consequently, a strength gradient may be created. In the transition point between the different joint types stops may therefore be formed. Due to the stops, the detachable joint may be detached until a predetermined aperture size without risking a rupture of the sanitary dressing or the detachment of the sheets forming the sheath.

In some examples, joints are continuous in the intermediate zone and discontinuous joints in the distal zone thereby further facilitating the aperture of the second opening. Furthermore, the size of the second opening may also be limited to the point where continuous joints start thereby creating stops. In addition, a complete separation of the sheath is prevented as the force necessary to detach continuous joints is greater than for discontinuous joints.

In some examples, the intermediate zone may be funnel-shaped to facilitate the insertion of the protruding portion of the catheter into the sheath and avoid the movements of the catheter within the sheath.

In some examples, the dressing may further comprise a removable protective sheet on the proximal zone to protect the adhesive, consequently the adhesive may be covered until the dressing is ready to be used.

In some examples, the proximal zone may have a peel value lower than 0.6 N/10 mm. This may help to easily detach the sanitary dressing from the primary dressing without causing the detachment of the primary dressing and/or without causing discomfort to the patient.

According to a further aspect, a sanitary dressing system is provided. The sanitary dressing system comprises: a primary dressing to fix a catheter protruding from a patient body through a skin entry site, and to cover the skin entry site; and a sanitary dressing according to any of herein disclosed examples.

In some examples of the sanitary dressing system, the primary dressing and the sanitary dressing may be independent from each other.

In some examples of the sanitary dressing system, the proximal zone may comprise a repositionable adhesive.

In some examples of the sanitary dressing system, the primary dressing may comprise a primary adhesive to be adhered to the skin, and the primary adhesive and the adhesive of the proximal zone may have different properties. Different properties may be related to different peel adhesion from a determined surface.

In some examples of the sanitary dressing system, the proximal zone may have a lower peel value than the primary dressing. The peel value of the primary dressing may be referred to the area of the primary dressing to be attached to the skin, for instance, between the area where the primary adhesive may be positioned and the skin.

In some examples of the sanitary dressing system, the proximal zone may have a greater MVTR value than the primary dressing. The MVTR value of the primary dressing may be referred to the area of the primary dressing to be attached to the skin, for instance, between the area where the primary adhesive may be positioned and the skin.

Throughout the present disclosure, the term system of the expression sanitary dressing system is to be understood as an arrangement, set, kit or the like.

Throughout the present disclosure, the term peel is to be understood as peel adhesion.

BRIEF DESCRIPTION OF THE DRAWINGS

Non-limiting examples of the present disclosure will be described in the following, with reference to the appended drawings, in which.

DETAILED DESCRIPTION

Figure 1:
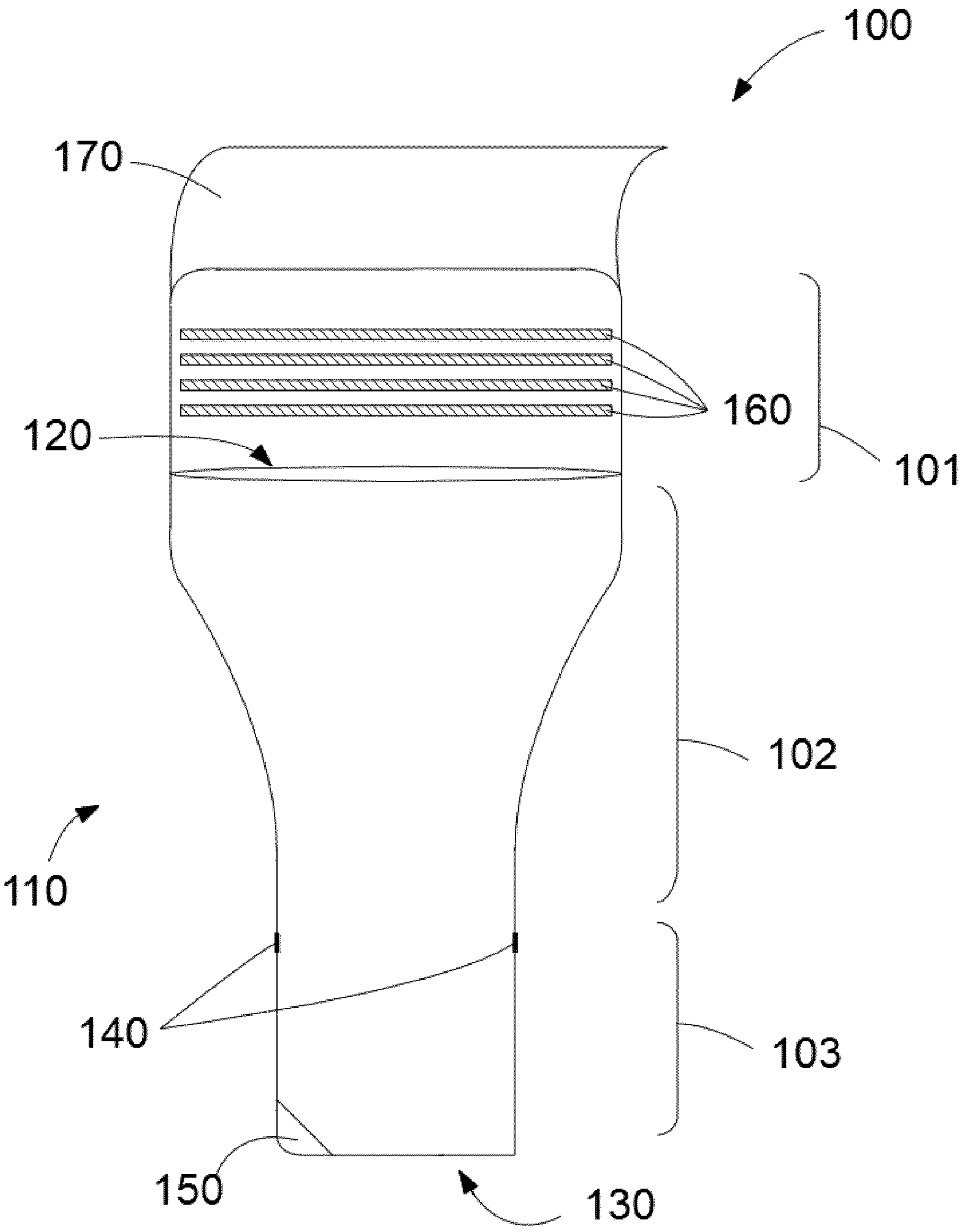
FIG. 1 schematically illustrates a top view of a sanitary dressing according to an example.

FIG. 1 shows a sanitary dressing 100 as seen from the side intended to contact a primary dressing adhered to the patient skin. The sanitary dressing 100 may comprise a proximal zone 101 to be arranged on a primary dressing, a distal zone 103 and an intermediate zone 102 arranged between the proximal zone and the distal zone.

The proximal zone 101 may comprise an adhesive 160 at the side facing the patient skin in order to adhere the dressing 100 to the primary dressing. The adhesive 160 may be applied forming a pattern in order to leave adhesive free portions thereby avoiding reducing the breathability of the primary dressing and so the patient skin is allowed to breath. In an example, the adhesive free portion may be of about 50% of the proximal zone.

The adhesive 160 may be applied in the proximal zone 101 directly creating a predetermined pattern. Alternatively, a continuous layer of adhesive 160 may be applied in the surface of the proximal zone, and the surface may afterwards be treated, e.g. perforated, transferred, laminated, etc., to remove part of the adhesive.

In an example, the pattern of the adhesive may comprise rhombus shaped spots. In an example, the adhesive may be arranged in a plurality of continuous or discontinuous strips thereby leaving adhesive free zones on the proximal zone 101 (see FIG. 1). The adhesive strips may be arranged longitudinally along almost the entire width of the proximal zone as shown in FIG. 1. In another example (not shown), the adhesive strips may be arranged vertically along the entire height of the proximal zone.

The adhesive 160 may be any adhesive compatible with the material of the primary dressing, e.g. polyurethane, and which maintains the adhesion capacity over the time. That is, an adhesive that once adhered does not increase the adhesion degree during the time that the sanitary dressing 100 remains adhered to the primary dressing. Therefore, the removal of the sanitary dressing may not cause the detachment of the primary dressing i.e. the primary dressing may not be pulled together with the sanitary dressing, and so unpleasant or painful detachments of the sanitary dressing are prevented. As a result, the pulling force exerted when the sanitary dressing is removed or repositioned does not affect patient comfort.

The adhesive 160 may be a repositionable adhesive e.g. acrylic or silicone based adhesive. A repositionable adhesive prevents an increase in the degree of adhesion of the adhesive, and therefore of the sanitary dressing, to the primary dressing over the time thereby reducing the possibility of detaching the primary dressing from skin interface when removing or repositioning the sanitary dressing 100. The possibility of breaking the sanitary dressing 100 upon removal or repositioning may therefore be prevented or at least substantially reduced. That is, by using a repositionable adhesive the use of an excessive pulling force when removing the sanitary dressing 100 from the primary dressing, may be prevented. The risk of hurting or causing discomfort to the patient may therefore be substantially reduced. Additionally, this repositionable adhesive enables repositioning of the sanitary dressing 100 as the dressing may be adhered and removed as many times as required to obtain a proper position i.e. a position receive the protruding portion of the catheter.

In an example, the adhesive 160 may be an acrylic adhesive, a polyurethane adhesive, a silicone adhesive, a hydrocolloid, a hotmelt or any other suitable adhesive material. In an example, for instance when the adhesive is acrylic based adhesive, the adhesive 160 may comprise a proportion of a plasticiser higher than conventional acrylic adhesives.

The viscoelastic properties of an adhesive may be defined by the Storage Modulus (G') that measures the ability of the adhesive to store energy, and wherein the greater value of G' the more elastic the adhesive is; by the Loss Modulus (G") that measures the ability of the adhesive to dissipate energy, and wherein, the greater value of G" the more viscous the adhesive is, and by the Loss Factor [tan(G"/G')] which is the ratio between G" and G'.

In an example, the adhesive 160 may have, at a temperature range between 34° C. and 37° C., a G' of about 6200-8000 Pa, more specifically of about 6450-7570 Pa; a G" of about 3500-8000 Pa, more specifically of about 3989-7436 Pa; and a tan(G"/G') of about 0.35-1.2, more specifically of about 0.62-0.99.

In addition, the proximal zone 101 may, once the adhesive is applied to it, have an elevated Moisture Vapour Transmission Rate (MVTR). By an elevated MVTR it is meant a value that allows enough skin transpiration during the use of the dressing, e.g. during 2-3 days. In an example, MVTR may be greater than 1500 g/($m^2$×24 h), that is, 1500 g per square meter per day, measured according standard EN 13726-2:2002.

By having an elevated MVTR in the proximal zone 101 the permeability of the primary dressing may not be affected, i.e. upon adhesion of the sanitary, dressing and so the skin of the patient may breathe in despite of having two overlapping dressings, i.e. the primary dressing and the proximal zone, adhered on it.

The proximal zone 101 may have a coat weight over 50 g/$m^2$. Such coat weight allows a proper adhesion of the sanitary dressing 100 to the primary dressing.

The sanitary dressing 100 may further comprise a removable release sheet 170 at the proximal zone 101 (shown almost removed in FIG. 1) to protect the adhesive until the dressing is to be adhered to primary dressing. In some examples, in order to facilitate its removal, the release sheet 170 may be split into two different sheets, and/or it may comprise a tab (not shown) that projects outwardly.

The dressing 100 may also comprise a sheath 110 arranged at both distal and intermediate zones 103, 102. The sheath 110 may be dimensioned to receive the protruding portion of a catheter 20 inserted into a patient body at a skin entry site 11 (see FIG. 2). In an example, the sheath 110 may comprise a width of about 20-80 mm, more specifically of about 52-54 mm; and a length of about 80-160 mmm, more specifically of about 153.5-157.5 mm. In some examples, the dimensions of the sanitary dressing may be reduced to better adapt to the catheter dimensions.

Figure 2:
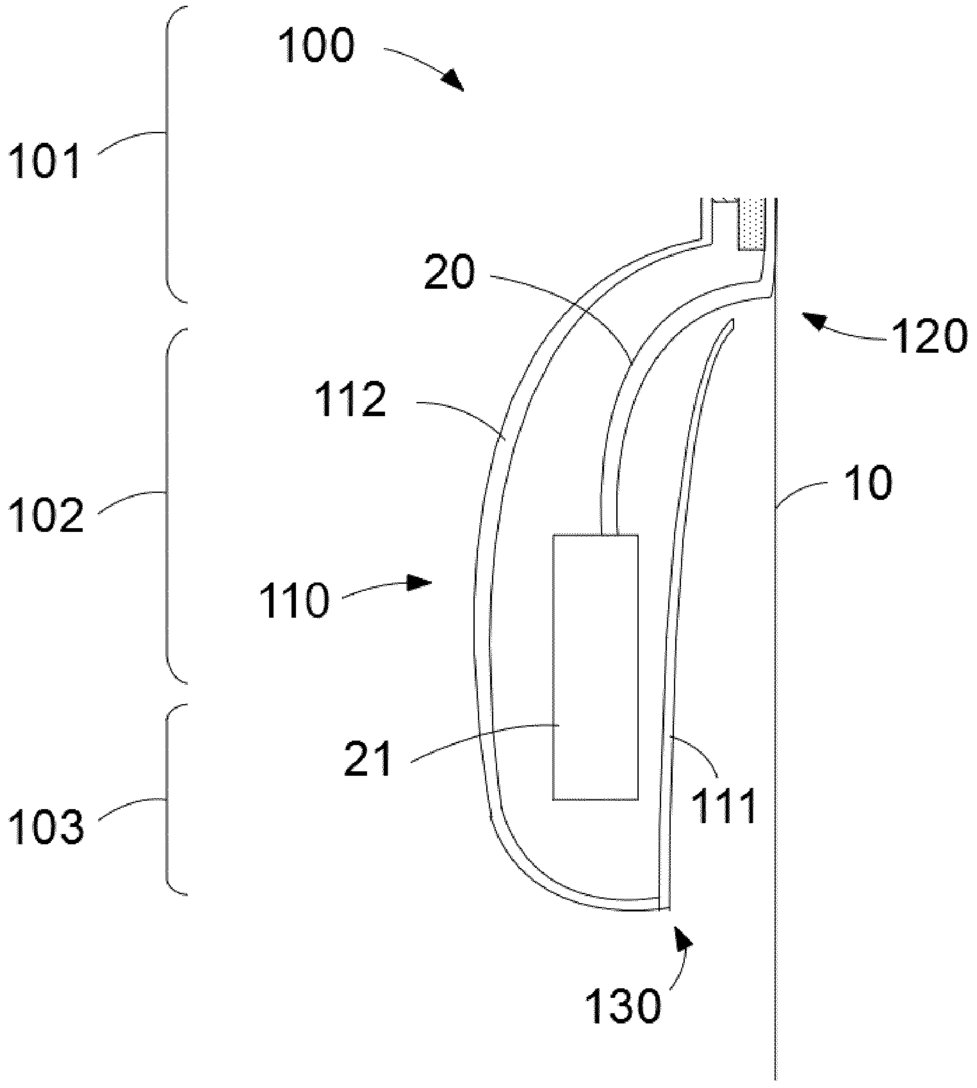
FIG. 2 schematically illustrates a very schematic lateral view of a sanitary dressing according to an example.

The sheath 110 may comprise an interior sheet 111 to be placed in contact with patient skin and an exterior sheet 112 which may be longer than the interior sheet in order to arrange the adhesive in the protruding portion of the exterior sheet, i.e. in the proximal zone 101 (see FIG. 2). In an alternative example, the interior and exterior sheets 111, 112 may be of the same length and the proximal zone 101 or the protruding portion, may be separately manufactured and afterwards coupled to the sheath.

The interior and exterior sheets 111, 112 may be joined together e.g. by adhesive, by ultrasonic welding, or by any other suitable method, thereby forming the sheath 110 comprising an inner cavity wherein the protruding portion of a catheter 20 may be housed. The sheets 111, 112 may be joined by joints at their edges, i.e. around almost the entire periphery, except where the exterior sheet starts protruding or overlapping the interior sheet wherein a first opening 120 may be formed.

The first opening 120 enables the catheter protruding portion to access the sheath 110 and be housed therein. The first opening 120 may be located at one end of the sheath 110 e.g. where the exterior sheet 112 extends beyond the interior sheet 111 (see FIG. 1). That is, the area in which the exterior sheet begins to protrude may be joint free in order to form the first opening. The first opening 120 of the sheath 110 may be arranged in order to be in correspondence with the protruding portion of the catheter once the sanitary dressing 100 is adhered to the primary dressing.

In an alternative example, the interior 111 and exterior 112 sheets may be joined to form a completely sealed sheath, i.e. comprising joints along the entire periphery. In such a case, the first opening 120 may be formed in the interior sheet 111 e.g. by performing a cut or removing part of the interior sheet 111.

Additionally, the interior and exterior sheets 111, 112 may also be joined to form a detachable joint 130 which may, upon its detachment, form a second opening through which, e.g. the sanitary staff, may easily gain access to the protruding portion of the catheter. The detachable joint 130 may be arranged at the distal zone 103 e.g. surrounding at least part of the periphery of the dressing. In other examples, the detachable joint may be arranged in a side wall of the sheath.

The type of joints that join the interior and exterior sheets 111, 112 together may vary in different zones of the sheath, i.e. along at least part of the periphery. In an example, the joints of the intermediate zone 102 may be continuous while the joints arranged at least in a portion of the distal zone 103 may be discontinuous thereby creating the detachable joint 130. Discontinuous joints may be easier to decouple and so facilitate the detachment of the detachable joint 130 while continuous joints may be stronger or more difficult to split apart to provide structural strength to the sheath. The access to the protruding portion of the catheter from the distal zone, i.e. by detaching or pulling apart the detachable joint, may therefore be easy and quick.

In addition, by having different joint types at the distal and the intermediate zones, stops 140 may be formed. The stops 140 may restrict the aperture of the second opening 130, i.e. of the detached detachable joint, by preventing the complete split up of the inner and exterior sheets. By using such stops the size of the second opening 130 may therefore be predetermined i.e. the detachable joint would only be detached up to the stops or up to the point in which the joints start to be continuous e.g. the limit between the intermediate and the distal zones.

The interior and exterior sheets 111, 112 may be made of a nonwoven breathable material and/or a material capable of being wrinkled but stiff enough to form a protective sheath, e.g. polypropylene, to facilitate pulling apart the interior and exterior sheets without damaging the dressing.

In some examples, the interior and exterior sheets 111, 112 the distal zone may comprise a pulling tab 150 to release both sheets and facilitate the detachment of the detachable joint.

The inner cavity of the sheath, i.e. the inner surfaces of both the inner and/or the exterior sheets, may be hydrophilic. A hydrophilic surface absorbs water or water-based compounds, e.g. blood or any corporal fluid secreted from the catheter port and/or the protruding portion of the catheter, and therefore may maintain the inner cavity dry. In an example, the sanitary dressing may further comprise an antiseptic coating e.g. polyhexanide, chlorhexidine, silver, etc. In an example, the inner surfaces of the sheath may comprise the antiseptic coating.

In addition, the exterior surfaces of the interior and exterior sheets 111, 112 may be hydrophobic or may comprise a hydrophobic coating to protect the dressing from external moisture.

As shown in FIG. 1, the width at least in some parts of the intermediate zone 102 may be more reduced than the width the proximal zone thereby preventing the movement of the protruding portion of the catheter within the sheath. In an example, the width along the intermediate zone may be progressively reduced e.g. the widest part of the sheath may be a 25% wider that the narrowest part. In an example, the intermediate zone may be funnel shaped. In another example, the intermediate zone may be bell shaped.

In an example (not shown), the sanitary dressing 100 may comprise an auxiliary fixation adhesive system. The auxiliary fixation adhesive system may be arranged at the intermediate zone or at the distal zone of the sanitary dressing to further prevent the movement of the dressing. In an example, the auxiliary fixation adhesive system may comprise a strip of an adhesive according to any of the disclosed examples. In an example, the auxiliary fixation system may be arranged at the sheath.

In some examples, the proximal zone 101 may have a peel value lower than 0.6 N/10 mm. This may mean 0.6 N for an adhesive tape of 10 mm wide.

A peel test was carried out by the inventors to compare a sanitary dressing according to any herein disclosed examples and some products available in the market. The peel test was performed in order to determine peel adhesion properties according to ISO 29862:2018. Particularly, the method 1 of said standard was implemented. Such method 1 is related to "Self adhesive tapes—Measurement of peel adhesion from stainless steel at an angle of 180°".

This method 1 provides a measurement of the force required to remove an adhesive tape that has been applied to a stainless steel plate at an angle of 180°. A length of adhesive tape is applied to the standard plate which is then fixed vertically in one of the jaws of a dynamometer. The other clamp pulls the free end of the adhesive tape at a 180° angle to the plate. The strength of the adhesive is measured by the force required to continuously peel the tape from the plate so that the separation line is perpendicular to the applied force.

The following table shows the obtained results. The term peel adhesion is used in the sense of the above mentioned ISO standard:

| Product | Peel adhesion (N/10 mm) |
|---|---|
| Oper cat pouch (IHT) | 0.36 |
| IV3000 ™ (S&N) | 0.90 |
| Tegaderm IV ™ (3M) | 2.06 |
| Tegaderm CHG ™ (3M) | 0.70 |
| Oper film protect IV (IHT) | 1.67 |

The first item "Oper cat pouch" may be related to a sanitary dressing according to the present disclosure, manufactured by the applicant (Iberhospitex S.A., in short IHT). The examples from the second to the fifth items may be characterized by a peel value greater than 0.6 N/10 mm to detach from the steel plate.

To make the peel test as similar as possible to an application of "Oper cat pouch", the inventors have carried out some tests having first placed the primary dressings (IV3000™, Tegaderm IV™, Oper film protect IV) to be used in combination with "Oper cat pouch" and on the ISO standard steel plate, obtaining the following average results:

| Product | Peel adhesion (N/10 mm) |
|---|---|
| Oper cat pouch (IHT) | 0.41 |
| Oper cat (IHT) | 2.72 |

"Oper cat" may be a sample dressing with a construction similar to the sanitary dressing 100 but with an adhesive of primary dressing 2 such as "Oper film protect IV", which has a conventional acrylic adhesive.

The results of the second table may mean that a primary dressing or a sanitary dressing with the adhesive of a primary dressing, attached to a primary dressing that is attached to the stainless steel plate may cause that the primary dressing is removed from the plate, and so the skin. However, the Oper cat pouch, as an example of herein disclosed sanitary dressing 100 with adhesive 160, may be detached from the primary dressing 2 without detaching the primary dressing from the plate or skin.

FIG. 2 depicts, in irregular proportions for the sake of clarity, a very schematic section view of a catheter exiting from a skin entry site 11 being covered by a primary dressing 2. In addition, the figure shows the sanitary dressing 100 of FIG. 1 adhered onto the primary dressing 2 wherein the sanitary dressing comprises the protruding portion of the catheter 20 housed inside the sheath 110. The figure represents only the cut along a plane perpendicular to the plane of the sanitary dressing 100, and therefore the sides along which the exterior and interior 111, 112 sheets are stitched or otherwise joined together are not shown.

In the figure, the sheath 110 is shown having the detachable opening 130 closed, that is, the detachable joint is shown undetached. FIG. 2 also shows the catheter protruding portion 20 passing through the first opening 120 to be housed within the sheath 110 of the sanitary dressing 100.

The catheter in this example comprises a connection port 21 to which several accessories e.g. an optical module, a fluid injector, etc., may be connected. In other examples, different catheter types may be used.

FIG. 2 further depicts adhesive strips 160 arranged at the proximal zone 101 being adhered to the primary dressing 2. Due to the elevated MVTR of the proximal zone 101 the skin 10 can breathe despite the overlap of the two dressings. The transpiration may therefore not be reduced which enhances the comfort of the patient.

Sanitary dressings such as the examples disclosed herein may be attached to a primary dressing 2 adhered to the skin of a patient after a catheter has been implanted at a skin entry site. As long as the protruding portion of the catheter need not be accessed, it may be enclosed within the sheath to prevent infections. The sanitary dressing 100 may be maintained in place until access to the catheter is required and then, the detachable joint may be detached. That is, when the catheter needs to be accessed, the detachable joint 130 may be detached and the protruding portion of the catheter may then be accessible for the sanitary staff e.g. to couple an accessory to the catheter port in order to provide a treatment. While the catheter is in use i.e. when a treatment is being administered, e.g. when drug is being injected, the dressing may remain adhered to the primary dressing.

In order to prevent infections, at the end of the treatment, the accessory may be disconnected from the catheter port, and in case the catheter is not supposed to be used in a short time e.g. for injecting a further treatment, the entire sanitary dressing may be removed and disposed, and be replaced by a new dressing having the detachable joint sealed. The primary dressing 2 may remain adhered to the patient skin e.g. 7 days, thereby protecting the skin entry site, while the sanitary dressing according to any of the disclosed examples may remain in place i.e. adhered to the primary dressing, for about 2-3 days. The removing frequency of the primary dressing may therefore be reduced and, in addition, the catheter protruding portion and the skin entry site may protected.

As seen in FIG. 2, a sanitary dressing system comprises a primary dressing 2 to fix a catheter 20 protruding from a patient body through a skin entry site 11, and to cover the sink entry site 11. The sanitary dressing system further comprises a sanitary dressing 100 according to any of herein disclosed examples.

In examples of the sanitary dressing system, the primary dressing 2 and the sanitary dressing 100 may be independent from each other. The sanitary dressing 100 may be attached to the primary dressing 2 through the adhesive 160.

In examples of the sanitary dressing system, the proximal zone 101 may comprise a repositionable adhesive. As herein disclosed, a repositioning of the sanitary dressing 100 on the primary dressing 2 may be allowed.

In examples of the sanitary dressing system, the primary dressing 2 may comprise a primary adhesive to be adhered to the skin 10, and the primary adhesive and the adhesive 160 of the proximal zone 101 may have different properties. Properties may be related to at least one of composition, pattern, coat weight, peel value, MVTR value or any combination thereof.

In examples of the sanitary dressing system, the proximal zone 101 may have a lower peel value than the primary dressing. By way of non-limiting example, the peel value of the primary dressing, for instance due to the features of primary adhesive, may be greater or higher than 0.6 N/10 mm.

In examples of the sanitary dressing system, the proximal zone 101 may have a greater MVTR value than the primary dressing. By way of non-limiting example, the MVTR value of the primary dressing may be due to, for instance, the features of primary adhesive. As herein mentioned, the skin of the patient may breathe in despite of having two overlapping dressings, i.e. the primary dressing and the proximal zone, adhered on it.

Although only a number of examples have been disclosed herein, other alternatives, modifications, uses and/or equivalents thereof are possible. Furthermore, all possible combinations of the described examples are also covered. Thus, the scope of the present disclosure should not be limited by particular examples, but should be determined only by a fair reading of the claims that follow. If reference signs related to drawings are placed in parentheses in a claim, they are solely for attempting to increase the intelligibility of the claim, and shall not be construed as limiting the scope of the claim.

The invention claimed is:

1. A sanitary dressing for protecting a portion of a catheter protruding from a patient body through a skin entry site, the sanitary dressing comprising:

a proximal zone to be arranged on a primary dressing which is in contact with patient skin, the proximal zone comprising an adhesive compatible with polyurethane for enabling repositioning of the sanitary dressing on the primary dressing, wherein the primary dressing is configured to fix the catheter, and the adhesive is configured to adhere the sanitary dressing to the primary dressing;

a distal zone and an intermediate zone between the proximal and distal zones, thereby forming a sheath for receiving the portion of the catheter.

2. The sanitary dressing according to claim 1, wherein the adhesive covers only part of the surface of the proximal zone.

3. The sanitary dressing according to claim 1, wherein the adhesive comprises a plurality of parallel adhesive strips.

4. The sanitary dressing according to claim 1, wherein the coat weight of the adhesive is over 50 $g/m^2$.

5. The sanitary dressing according to claim 1, wherein the proximal zone has a MVTR greater than 1500 $g/(m^2 \times 24\ h)$.

6. The sanitary dressing according to claim 1, wherein the adhesive has, at a temperature range between 34° C. and 37° C., a Storage Modulus (G') of about 6200-8000 Pa; a Loss Modulus (G") of about 3500-8000 Pa; a Loss Factor [tan (G"/G')] of about 0.35-1.2.

7. The sanitary dressing according to claim 1, wherein the sheath comprises:

a first opening arranged between the proximal zone and the intermediate zone for enabling the portion of the catheter protruding from the skin entry site to be received in the sheath; and a detachable joint closing the distal zone and forming a second opening upon detachment.

8. The sanitary dressing according to claim 7, wherein the sanitary dressing comprises an exterior sheet and an interior sheet joined by joints in the intermediate zone and in the distal zone for forming the sheath.

9. The sanitary dressing according to claim 8, wherein the joints of the distal zone are different from the joints of the intermediate zone such that the joints of the intermediate zone form stops that limit an aperture of the second opening upon detachment of the detachable joint.

10. The sanitary dressing according to claim 8, wherein the joints of the intermediate zone are continuous and the joints of the distal zone are discontinuous.

11. The sanitary dressing according to claim 1, wherein the sheath comprises an auxiliary fixation adhesive system.

12. The sanitary dressing according to claim 1, wherein the sheath comprises a material from at least one of hydrophobic, impermeable or superhydrophobic.

13. The sanitary dressing according to claim 1, wherein the intermediate zone is funnel-shaped or bell-shaped.

14. The sanitary dressing according to claim 1, wherein the proximal zone has a peel value lower than 0.6 N/10 mm.

15. A sanitary dressing system comprising:

a primary dressing to fix a catheter protruding from a patient body through a skin entry site, and to cover the skin entry site;

a sanitary dressing for protecting a portion of the catheter protruding from a patient body through a skin entry site, the sanitary dressing comprising:

a proximal zone to be arranged on the primary dressing which is in contact with patient skin, the proximal zone comprising an adhesive compatible with polyurethane for enabling repositioning of the sanitary dressing on the primary dressing;

a distal zone and an intermediate zone between the proximal and distal zones, thereby forming a sheath for receiving the portion of the catheter.

16. The sanitary dressing system according to claim 15, wherein the primary dressing and the sanitary dressing are independent from each other.

17. The sanitary dressing system according to claim 15, wherein the proximal zone comprises a repositionable adhesive.

18. The sanitary dressing system according to claim 15, wherein the primary dressing comprises a primary adhesive to be adhered to the skin, and the primary adhesive and the adhesive of the proximal zone have different properties.

19. The sanitary dressing system according to claim 15, wherein the proximal zone has a lower peel value than the primary dressing.

20. The sanitary dressing system according to claim 15, wherein the proximal zone has a greater MVTR value than the primary dressing.

* * * * *